United States Patent [19]

Geissler et al.

[11] 4,077,772

[45] Mar. 7, 1978

[54] METHOD FOR THE DETERMINATION OF HEMOGLOBIN IN TRACE AMOUNTS

[75] Inventors: Ulrich C. Geissler, Cary; William J. Stith, Mundelein; Kathleen J. Jewett, Waukegan, all of Ill.

[73] Assignee: Baxter Travenol Laboratories, Inc., Deerfield, Ill.

[21] Appl. No.: 801,887

[22] Filed: May 31, 1977

[51] Int. Cl.$^2$ .......................................... G01N 33/16
[52] U.S. Cl. .................................. 23/230 B; 252/408
[58] Field of Search ..................... 23/253 TP, 230 B; 252/408; 424/7

[56] References Cited

U.S. PATENT DOCUMENTS

| | | | |
|---|---|---|---|
| 3,663,175 | 5/1972 | Depositar | 23/230 B |
| 3,677,707 | 7/1972 | Pride et al. | 23/230 B |
| 3,975,161 | 8/1976 | Svoboda et al. | 23/230 B |
| 4,017,261 | 4/1977 | Svoboda et al. | 23/253 TP |

OTHER PUBLICATIONS

Crosby et al., Blood 11:380 (1956).
Holland et al., Tetrahedron 30:3299 (1974).

Primary Examiner—R.E. Serwin
Attorney, Agent, or Firm—Henry W. Collins; Paul C. Flattery; Garrettson Ellis

[57] ABSTRACT

An improved technique for determining the presence of hemoglobin, having increased sensitivity, is provided by bringing the material to be tested into contact with an acidic solution of tetramethylbenzidine and hydrogen peroxide to form a mixture, allowing said mixture to stand for a predetermined period of time, and thereafter examining the mixture for the presence of a colored complex indicative of the presence of hemoglobin. Organic acid is present in a concentration generally of at least 30 percent by volume, to provide a pH of no more than about 2.

14 Claims, No Drawings

METHOD FOR THE DETERMINATION OF HEMOGLOBIN IN TRACE AMOUNTS

BACKGROUND OF THE INVENTION

Benzidine has been used in a method for the microdetermination of hemoglobin in blood plasma, serum, or other fluids, as in the procedure of Crosby and Furth described in Blood 11:380 (1956). However, benzidine is extremely carcinogenic, and thus has been recently rendered unavailable for routine laboratory use.

As reported by Holland, et. al. in Tetrahedron 30:3299 (1974) it has been proposed to substitute for benzidine the compound 3,3'5,5'-tetramethylbenzidine, which appears to be non-carcinogenic, and yet which, in the presence of hydrogen peroxide, forms a highly-colored complex with hemoglobin. However, the procedure, as suggested by Holland, et al. is insufficiently sensitive to quantitatively determine trace amounts of hemoglobin on the order of 10 milligram percent and less.

Accordingly, the Holland, et al. test is generally unsuitable for testing for the presence of trace amounts of hemoglobin in blood plasma taken from stored blood, for example as a determination of the viability of the bood. As blood deteriorates, hemoglobin is released into the plasma by dying blood cells. Thus a quantitative analysis of the hemoglobin present in such plasma is an index of the viability of the blood.

In accordance with this invention, a significant improvement in sensitivity has been accomplished by performing the hemoglobin test with a benzidine derivative and hydrogen peroxide in a mixture at an acid content which is greater than that which has been used in the prior art relating to hemoglobin testing with this benzidine derivative. The result of this appears to be the production of a different, green complex material with hemoglobin (the hemoglobin complex in the prior art is blue or blue-green) which is capable of being analyzed in concentrations as low as on the order of 1 milligram of hemoglobin per 100 ml. of the solution to be tested. This is indeed far lower than that available for the prior art. Furthermore, this invention can be utilized to provide a complex which has good stability at the endpoint, to permit reading of the endpoint over a significant period of time, rather than one specific moment.

By this invention, the sensitivity of the method is adjustable so that the quantitative presence of hemoglobin can be determined photometrically over a significant, highly dilute range of concentrations, for example, from 1 to 30 mg. of hemoglobin per 100 ml. of solution, by proper adjustment of the pH and other factors.

DESCRIPTION OF THE INVENTION

In accordance with this invention, the method of determining the presence of hemoglobin in a material comprises bringing the material into contact with an acidic solution of a benzidine derivative such as tetramethylbenzidine, and hydrogen peroxide, to form a mixture; allowing said mixture to stand for a predetermined period of time, and examining said mixture for the presence of a colored complex indicative of the presence of hemoglobin. In the improvement of this invention, the acidic solution has a pH of preferably no more than 2, with the specific preferred range being on the order of 0.8 to 1.5, for the greatest sensitivity to hemoglobin. The acid, and preferably organic acid, is present in a concentration of at least 30 percent by volume, and preferably from 35 to 50 percent in the test mixture.

Preferably, the acidic conditions of the solution are provided by the presence of acetic acid in this method, although it is believed that other acids, and especially organic acids such as lactic acid, propionic acid, butyric acid, tartartic acid, citric acid, or fumaric acid are also usable, to achieve the desired concentration and pH.

The hydrogen peroxide is preferably present in a concentration of about 0.2 to 3 percent (weight/volume). With reduced hydrogen peroxide concentrations, a longer incubation time is necessary for the endpoint of the reaction to be reached. For example, for a 0.5 percent hydrogen peroxide concentration an incubation time at room temperature of about 20 to 30 minutes, after addition of the various ingredients and the unknown material to be tested, is required. However, the colored complex which results remains stable for approximately 10 to 15 minutes under the reaction conditions, which makes the reading of the endpoint an easier matter.

At concentrations of about 1 percent hydrogen peroxide, the incubation period at room temperature is decreased to about 10 to 20 minutes. However, the resulting complex formed with hemoglobin tends to be less stable, and should be read within about two minutes after the incubation period in order to avoid a false quantitative reading due to deterioration of the complex.

The benzidine derivative, preferably tetramethylbenzidine, is desirably present in the acidic solution in a concentration of 0.05 to 1.5 percent (weight/volume) and preferably 0.2 to 0.3 percent.

With respect to the pH of the system, the greatest sensitivity of detection of the colored complex of hemoglobin is found, for example, when the test solution is at least about 45 percent (weight/volume) acetic acid. At this concentration, from 1 to 30 mg. of hemoglobin per 100 ml. solution can result in an intense green color which can be photometrically analyzed on a quantitative basis. A preferred wavelength for photometric analysis in 375 millimicrons.

However, with this pH, if the hemoglobin is present in concentrations greater than about 30 milligrams per 100 ml. of solution, the color endpoint is so intense that it may become difficult to quantitatively measure the presence of hemoglobin under the specific reaction conditions described above.

When about 25 to 35 percent acetic acid is present in the test solution, less color sensitivity is achieved than in the previously described formulation. However, with a hydrogen peroxide concentration of 0.2 to 3 percent, and preferably no more than about 1 percent, this system is capable of quantitatively determining at least about 5 mg. hemoglobin, and up to and beyond 30 mg. of hemoglobin per 100 ml. of solution. Also, the complex generated to provide the quantitative endpoint is more stable in terms of its color duration.

The green complex of this invention may be formed at at least a 30 percent acetic acid concentration, in the presence of hemoglobin.

Another desirable system within the scope of this invention is with 37.5 percent (weight/volume) acetic acid in the test solution. This system is capable of detecting a quantitative endpoint throughout a range of about 5 to 40 mg. of hemoglobin per 100 ml. of solution when read photometrically, for example at 375 millimicrons.

All of the above test systems are, of course, also able to detect higher concentrations of hemoglobin on at least a qualitative basis.

It is generally preferred to photometrically read the endpoint provided by the test systems of this invention at a wavelength between 370 to 380 millimicrons, (specifically looking for a peak near 375 millimicrons) although readings may also be made at about 460 and 655 millimicrons.

The stability of the complex at endpoint can be increased by diluting the mixture after endpoint with a pH increasing solution, such as 1 percent acetic acid or water, to put the pH in a less acidic range, and to dilute the acid concentration.

Accordingly, by the method of this invention, very small traces of hemoglobin can be detected, both for medical purposes, such as the hemoglobin analysis of plasma in stored blood, and for other general purposes such as the determination of trace amounts of blood for purposes of crime detection or the like.

The examples below are not intended to limit the scope of the invention of this application, but are provided purely as specific illustrations thereof, the scope of the invention being as defined in the claims below.

EXAMPLE 1

To a mixture of 75 ml. of glacial acetic acid and 25 ml. of distilled water (75 percent acid solution) was added 500 mg. of 3,3'5,5'-tetramethylbenzidine.

To 1 ml. of this mixture was added 20 microliters of centrifuged, cell-free blood plasma from outdated blood, and 1 ml. of 1 percent (weight/volume) hydrogen peroxide solution in distilled water. The resulting solution contained about 37.5 percent of acetic acid, 0.5 percent of hydrogen peroxide, and 0.25 percent (weight/volume) of the 3,3'5,5'-tetramethylbenzidine per liter.

This mixture was incubated for about 25 to 30 minutes at room temperature, and then the optical density was read photometrically at 375 millimicrons. The results were compared with reference samples of hemoglobin of known concentration in blood plasma simultaneously prepared in the manner described above.

The quantitative amount of hemoglobin, if any, present in the unknown, was determined by photometric comparison with the reference samples which were simultaneously prepared.

In this present instance, hemoglobin concentrations in unknown samples were determined, by comparison with the reference samples, to have concentrations, respectively, of 2.6 mg., 10.9 mg., and 33.1 mg. per 100 ml. of test solution, by the presence of a deep green color, indicating the presence of hemoglobin.

As alternate conditions to the above, generally corresponding results can be achieved by the substitution of 50 to 1000 mg. of the tetramethylbenzidine material for the 500 mg. of the material specifically utilized above.

Similarly, the acetic acid preferably can have a concentration of 35 to 45 percent (weight/volume) or any percentage in between, as desired.

Also, the hydrogen peroxide concentration can be adjusted as desired. As described above, when a 1 percent hydrogen peroxide concentration is utilized, the incubation period is reduced to 10 to 20 minutes, and the endpoint should be read quickly at the end of the incubation period.

EXAMPLE 2

The experiment of Example 1 was repeated, except that an equivalent amount of 90 percent acetic acid solution was substituted for the 75 percent acetic acid utilized above, to give a final solution concentration of 45 percent. The resulting test system was found to be capable of quantitative determination of hemoglobin concentrations of 1 to 10 mg. of hemoglobin per 100 ml. by spectrophotometric determination at 375 millimicrons, in comparison with a standard curve as in the previous example.

EXAMPLE 3

When the experiment of Example 1 is repeated, except that 30 percent acetic acid solution is utilized rather than the 37.5 percent acetic acid, this test solution provides a relatively stable endpoint, and is capable of quantitatively determining hemoglobin concentrations from about 5 to 30 mg. of hemoglobin per 100 ml., when spectrophotometrically determined against a standard curve at 375 millimicrons. In this instance, an incubation period of about 30 to 40 minutes is preferable.

EXAMPLE 4

The experiment of Example 1 was repeated with the added step of diluting the reaction mixture after the twenty-five to thirty minute incubation period with about 10 ml. of 1 percent acetic acid. This technique is capable of the quantitative determination of hemoglobin concentrations of about 2.5 to 40 mg. of hemoglobin per 100 ml., with the green complex thus formed being of substantially increased stability to permit delayed and careful spectrophotometric determination.

EXAMPLE 5

Equivalent results are obtained from the substitution of the 500 mg. of 3,3'5,5'-tetramethylbenzidine utilized in Example 1 with 700 mg. of the same material, followed by dilution of the reaction mixture after the 25 to 30 minute incubation period with 10 ml. of 1 percent acetic acid solution.

That which is claimed is:

1. The method of determining the presence of hemoglobin in a material which comprises: bringing said material into contact with an organic acid solution of tetramethylbenzidine and hydrogen peroxide to to form a mixture, allowing said mixture to stand for a predetermined period of time, and examining said mixture for the presence of a green colored complex indicative of the presence of hemoglobin, the improvement comprising:

said organic acid being present in said solution concentration of at least 35 percent by volume.

2. The method of claim 1 in which from 0.2 to 3 percent (weight/volume) of hydrogen peroxide is present.

3. The method of claim 1 in which said acidic solution contains acetic acid at a concentration of essentially 35 to 50 percent.

4. The method of claim 1 in which the pH of said acidic solution is from 0.8 to 1.5.

5. The method of claim 1 in which said tetramethylbenzidine is present in said acidic solution in a concentration of 0.05 to 1.5 percent (weight/volume).

6. The method of claim 1 in which after said predetermined period of time, aqueous solution is added to dilute color and stabilize the reaction by reducing the acid concentration of said solution.

7. An aqueous solution for determining the presence of hemoglobin in a material which comprises: from 0.05 to 1.5 percent (weight/volume) of tetramethylbenzidine, from 0.2 to 3 percent of hydrogen peroxide, and organic acid in a concentration of 35 to 50 percent by volume.

8. The solution of claim 7 in which said pH is from 0.8 to 1.5.

9. The solution of claim 7 in which said concentration of hydrogen peroxide is essentially from 0.5 to 1 percent (wt./vol.).

10. The solution of claim 7 in which said tetramethylbenzidine is present in a concentration of about 0.2 to 0.3 percent (wt./vol.).

11. The method of determining the presence of hemoglobin in a material which comprises: bringing said material into contact with an organic acid solution of tetramethylbenzidine and hydrogen peroxide to form a mixture, allowing said mixture to stand for a predetermined period of time, and examining said mixture for the presence of a color complex indicative of the presence of hemoglobin, the improvement comprising: said organic acid being present in a concentration of 30 to 50 percent by volume, there being from 0.2 to 3 percent (wt./vol.) of hydrogen peroxide present.

12. The method of claim 11 in which said tetramethylbenzidine is present in said acidic solution in a concentration of 0.05 to 1.5 percent (wt./vol.).

13. The method of claim 12 in which said organic acid is acetic acid.

14. An aqueous solution for determining the presence of hemoglobin in a material which comprises an organic acid in a concentration of 30 to 50 percent by volume, from 0.2 to 3 percent (wt./vol.) of hydrogen peroxide, and from 0.05 to 1.5 (wt./vol.) of tetramethylbenzidine.

* * * * *